United States Patent
Beausoleil et al.

(10) Patent No.: US 8,673,217 B2
(45) Date of Patent: Mar. 18, 2014

(54) SENSOR USING PLASMON RESONANCE

(75) Inventors: Raymond G. Beausoleil, Redmond, WA (US); Wei Wu, Mountain View, CA (US); David A. Fattal, Mountain View, CA (US); Marco Fiorentino, Mountain View, CA (US)

(73) Assignee: Hewlett-Packard Development Company, L.P., Houston, TX (US)

( * ) Notice: Subject to any disclaimer, the term of this patent is extended or adjusted under 35 U.S.C. 154(b) by 1899 days.

(21) Appl. No.: 11/975,538

(22) Filed: Oct. 18, 2007

(65) Prior Publication Data

US 2009/0103095 A1 Apr. 23, 2009

(51) Int. Cl.
*G01N 21/00* (2006.01)

(52) U.S. Cl.
USPC .................................... 422/82.05; 359/585

(58) Field of Classification Search
USPC .................................... 422/82.05; 359/585
See application file for complete search history.

(56) References Cited

U.S. PATENT DOCUMENTS

| 3,971,065 | A | 7/1976 | Bayer |
| 7,153,720 | B2 | 12/2006 | Augusto |
| 7,248,297 | B2 | 7/2007 | Catrysse et al. |
| 2003/0103150 | A1 * | 6/2003 | Catrysse et al. ............... 348/272 |
| 2010/0046077 | A1 * | 2/2010 | Lee et al. ....................... 359/585 |

OTHER PUBLICATIONS

Santhanam et al., Microcontact Printing of Uniform Nanoparticle Arrays, 2004, Nano Letters, vol. 4 No. 1, pp. 41-44.*
Reddy, Vanga R., "Gold Nanoparticles: Synthesis and Applications" SYNLETT 2006, No. 11, pp. 1791-1792.
Schaadt, D.M. et al., "Enhanced Semiconductor Optical Absorption Via Syrface Plasmon Excitation in Metal Nanoparticles" App. Physics Letters (2005) 86, 063106-1 to 063106-3.

* cited by examiner

*Primary Examiner* — Jonathan Hurst

(57) ABSTRACT

A sensing system can include one or more particles having one or more plasmon resonances. The particles can be positioned adjacent to the active region of a sensor to enhance the sensitivity of the sensor to electromagnetic radiation having frequencies corresponding to the plasmon resonances. An array of sensors such as used for color imaging can employ different types of particles adjacent to different sensors, so that different sensors sense different colors. During fabrication of such sensors, the particles can be applied mechanically or using a process such as inkjet printing.

7 Claims, 2 Drawing Sheets

SENSOR USING PLASMON RESONANCE

BACKGROUND

A color image sensor for a digital camera or other device normally contains a color filter array (CFA) or color filter mosaic (CFM) that overlies an array of light sensors. FIG. 1, for example, illustrates a conventional color image sensor 100 including a sensor array 110 with an overlying CFA 120. Sensor array 110 can be an integrated semiconductor device such as a charge-coupled device (CCD) sensor array or a complementary metal-oxide-semiconductor (CMOS) image sensor. CFA 120 in the example of FIG. 1 is a Bayer or GRGB filter, which is a rectangular array of green, red, and blue color filters arranged such that each color filter that is not on the edge of CFA 120 is surrounded by four green filters, two red filters, and two blue filters. Pixel sensors 112 under respective color filters of CFA 120 can integrate the energy of light transmitted through the respective color filters to measure the intensities of incident green, red, or blue light. Each of these measurements indicates a color component (e.g., green, red, or blue level) of a pixel corresponding to that pixel sensor 112. A process commonly referred to as demosaicing can then determine other color components of pixels through interpolations using the color components measured by neighboring pixel sensors.

CFAs such as CFA 120 can be manufactured on sensor arrays using integrated circuit fabrication techniques to fabricate each color-specific optical filter. Such optical filters come in different types. The most common optical filters are absorptive filters and reflective filters. Absorptive optical filters absorb the undesired wavelengths of light so that only the wavelength or wavelengths of interest are transmitted through the filter. Thus, absorptive optical filters must be thick enough (e.g., at least several wavelengths thick) to allow efficient absorption of the undesired wavelengths. In contrast, reflective optical filters reflect undesired wavelengths of light. Reflective optical filters can be made using thin film dielectric layers stacks, which provide accurate control over the filter central frequency and spectral width. Fabrication of reflective optical filters can be quite expensive and generally requires tight control of the film thicknesses. Simpler thin structures and fabrication processes for color image sensors would be desirable.

SUMMARY

In accordance with an aspect of the invention, a sensing system can include one or more particles having one or more plasmon resonances. The particles are positioned in or adjacent to the active region of a sensor so that the plasmon resonances enhance the sensitivity of the sensor to electromagnetic radiation having frequencies corresponding to the plasmon resonances.

DETAILED DESCRIPTION

In accordance with an aspect of the invention, the efficiency with which a sensor detects desired frequencies of light can be enhanced by adding particles that create plasmon resonances at the desired frequencies. In a color image sensor, for example, nanoparticles with different properties or different surrounding materials can be tuned to have plasmon resonances at the frequencies corresponding to specific colors, and the nanoparticles can be positioned in, on, or near photoactive regions of pixel sensors. The plasmon resonances greatly increase resonant electromagnetic oscillations in the active regions and thereby enhance the efficiency with which the active regions absorb light with frequencies matching the plasmon resonances. The pixel sensors with associated nanoparticles can thus be configured to measure different color components and can replace the pixel sensor using color filters in applications such as color image sensors. In one embodiment, the light sensitive region in each pixel is made thin enough that without plasmon enhancement, the quantity of electron-hole pairs generated during a specific time interval within the photoactive layer is below the noise level. Therefore, although light at all frequencies is transmitted through the sensor, only the light component resonating with the adjacent particles will induce the generation of detectable carriers in the sensor. No optical filter is needed, which reduces the number of elements of the device and alleviates the need for alignment of the optical filters to their respective detectors. Moreover, since the light sensors themselves may have reduced physical dimensions, the light sensors will typically have reduced capacitance, a shorter transit time for carriers, and lower operating power, which translates into a faster image acquisition rate and less power consumption. Finally, nanoparticles of different types can be applied to different sensors in a sensor array using low-cost high-throughput techniques such as inkjet printing.

Figure 2:
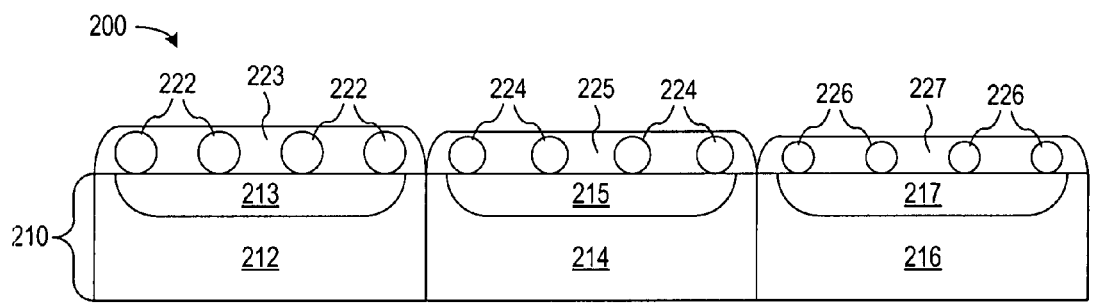
FIG. 2 shows a cross-sectional view of a portion of an image sensor in accordance with an embodiment of the invention using particles overlying photoactive regions to enhance sensing of specific frequency bands.

FIG. 2 shows a cross-section of a portion of an image sensor 200 in accordance with an embodiment of the invention. Image sensor 200 would typically be used in a digital camera or a camcorder where an optical system (not shown) forms an image on a surface of image sensor 200. Image sensor 200 includes a sensor array 210, which is an array containing pixel sensors 212, 214, and 216. Only three pixel sensors 212, 214, and 216 are shown in FIG. 2 for ease of illustration, but in a typical embodiment sensor array 210 may contain millions of pixel sensors arranged with thousands of pixel sensors in each row or column. In general, sensor array 210 can be of any design that provides discrete pixel sensors 212, 214, and 216 and may, for example, be a CCD image sensor or a CMOS image sensor, which are well known and currently employed in digital cameras and camcorders.

Pixel sensors 212, 214, and 216 may all be substantially identical and have a high-pass sensitivity to a broad spectrum of light frequencies as is common for current semiconductor light sensors. Many designs for individual pixel sensors 212, 214, and 216 are known in the art. The particular construction of pixel sensors 212, 214, and 216 is not critical to the present invention, except that each pixel sensor 212, 214, and 216 includes respective photoactive regions 213, 215, and 217. Photoactive regions 213, 215, and 217 can be doped semiconductor regions of photodiodes in respective pixel sensors 212, 214, and 216. When exposed to light, reverse biased photodiodes in a pixel sensor 212, 214, or 216 will conduct a current having a magnitude that generally indicates the rate at which the photoactive region absorbs photons to create electron-hole pairs. Pixel sensors 212, 214, and 216 can thus use the current through a photodiode to measure the intensity of incident light capable of producing electron-hole pairs.

Active regions 213, 215, and 217 in image sensor 200 can be made smaller and/or thinner than typical photoactive regions in current image sensors because the use of plasmon resonances, as described further below, enhances photon absorption. Pixel sensors generally must be large enough that the detected number of photons per second per pixel stays sufficiently above the noise threshold. This means that the photoactive regions in conventional pixel sensors must be more than about 1 $\mu m^2$ in area and about 1 $\mu m$ thick. The minimum size for conventional pixel sensors limits the resolution of image sensors and is a major reason for mosaicing, particularly because a pixel sensor having laterally arranged subpixels would be even larger and provide lower resolution. With photon detection efficiency enhanced using plasmon resonances, the active regions 213, 215, and 217 can be as small as about 100 nm in width and about 100 nm thick or less. The smaller sensor size permits much smaller pixel sensors 212, 214, and 216, increasing resolution through smaller pixel areas, decreasing the cost of the image sensor by allowing fabrication of more image sensors per wafer, and increasing speed through lower capacitances and shorter current paths. The higher resolution in turn allows use of much simpler demosaicing algorithms. An alternative approach to provide high resolution image sensors would be the Foveon three-layer camera sensor, which doesn't require mosaicing but is expensive.

Particles 222 are adjacent to photoactive region 213 in pixel sensor 212 and are constructed and placed to create one or more specific plasmon resonances in the environment adjacent to photoactive region 213. The plasmon resonances created by particles 222 correspond to the frequencies of light that pixel sensor 212 is intended to measure. For example, particles 222 can create resonances at frequencies corresponding to red light. The plasmon resonances increase the magnitude of electromagnetic oscillations at or near the resonant frequencies and extend the interaction time of active region 213 with photons having the resonant frequencies and therefore increase the efficiency with which those selected frequencies are absorbed in active region 213. To facilitate this enhancement, particles 222 are preferably close to active region 213 (e.g., within about a wavelength of the measured light).

Many types of particles exhibiting plasmon resonances in the visible spectrum are known. For example, particles 222 can be solid or hollow spheres of a metal such as gold or silver and having a diameter of about 10 to 100 nm. Spherical nanoparticles having precisely controlled diameters can be fabricated using known techniques including colloidal techniques or electrochemical deposition of metal into membrane pores or onto other surfaces. See, for example, V. R. Reddy, "Gold Nanoparticles: Synthesis and Applications" (2006), p. 1791, and references therein. Particles of other shapes or made of other metals or composites of metals and other materials are also known to have plasmon resonances and could be used in sensor 200. In general, the plasmon resonances exhibited by such particles depend on the size of the particles (e.g., the diameter of a spherical particle), the composition of the particles, and the dielectric properties of the surroundings of the particles. For example, the size and composition of particles 222 may be selected according to the desired plasmon resonances, but the plasmon resonances created by particles 222 when affixed on pixel sensor 212 will also be influenced by the dielectric properties of sensor 212, the dielectric properties of other materials including a binding material 223 around particles 222, and the spacing of particles 222 relative to each other. The characteristics that influence the plasmon resonances will be subject to variations that are controllable during or inherent to manufacturing processes, and these variations generally serve to broaden the plasmon resonance, which may be desirable for a pixel sensor that measures a spectral band of incident light.

Binding material 223 acts as an adhesive to hold particles 222 in the desired position adjacent to active area 213. Binding material 223 may be an organic resin or any suitable substance capable of application and adherence to sensor array 210. In general, the dielectric properties of binding material 223 should be taken into account when selecting the type of particles 222 to provide a desired plasmon resonance. In a typical application, a region containing binding material 223 and particles 222 over a sensor 212 may be about 400 nm wide and about 100 nm thick. FIG. 2 illustrates particles 222 as being immersed in binding material 223, but binding material 223 can alternatively be a thin layer that adheres to the surface of sensor array 210 and only a bottom portion of each particle 222.

Particles 222 as mentioned above can have size, spacing, and surrounding structures 223 and 213 selected to provide a plasmon resonance with a desired peak frequency and a desired resonance width. In an exemplary embodiment, particles 222 create a plasmon resonance corresponding to a band of red light so that underlying pixel sensor 212 has greater sensitivity to and predominantly measures red light. Pixel sensors 214 and 216 in FIG. 2 respectively have particles 224 and 226 overlying their respective active regions 215 and 217. Particles 222, 224, and 226 can all be of different types selected to create different plasmon resonances adjacent to active regions 213, 215, and 217. For example, in the exemplary embodiment, particles 224 in associated binding material 225 create a plasmon resonance corresponding to a band of green light, and particles 226 in associated binding material 227 create a plasmon resonance corresponding to a band of blue light. In general, shorter wavelength plasmon resonances can be created using smaller particles, e.g., spherical particles with smaller diameters. However, the spacing of particles 224 or 226 and the dielectric properties of their respective surroundings (e.g., binding materials 225 and 227) can be selected according to the desired plasmon resonances.

Figure 1:
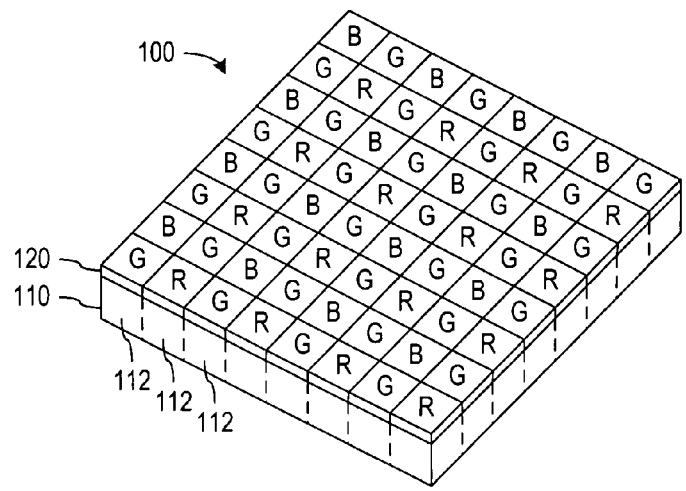
FIG. 1 shows a portion of a conventional color image sensor.

Pixel sensors 212, 214, and 216 in the exemplary embodiment of image sensor 200 respectively measure red, green, and blue light. Similar red, green, and blue sensors can be arranged in a mosaic, e.g., a GBGR array similar to the arrangement of the color filters in FIG. 1. A conventional demosaicing process can then use the measurement of intensities of red, green, and blue light at different pixel sensors 212, 214, and 216 in sensor array 210 to determine the colors of each pixel in an image formed on color image sensors 200. Pixel sensors similar to sensors 212, 214, and 216 could alternatively be tuned to detect different colors, e.g., cyan, yellow, green, and magenta, and/or be in a pattern that may used in another type color filter array. Alternatively, a pixel sensor can include sensors 212, 214, and 216 as subpixels that directly measure color components of a pixel, while the small size of sensors 212, 214, and 216 provides a relatively high resolution even when subpixels are laterally arranged.

Figure 3:
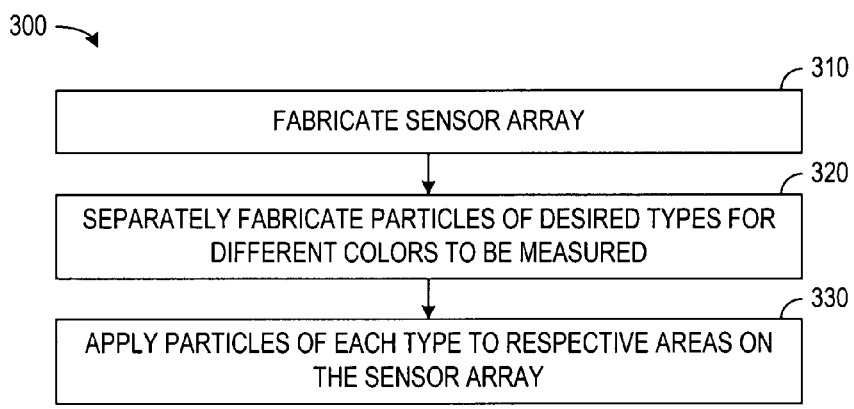
FIG. 3 is a flow diagram of a fabrication process in accordance with an embodiment of the invention.

FIG. 3 is a flow diagram of a process 300 for fabricating an image sensor such as image sensor 200 of FIG. 2. Process 300 begins with a step 310 of fabricating a sensor array such as sensor array 210. Conventional integrated circuit processing techniques can be used to fabricate the sensor array as a CCD sensor array or a CMOS sensor array. Fabrication step 310 does not need to form a color filter array (CFA) and accordingly may be simpler and less costly than processes using IC fabrication techniques to fabricate a CFA. Additionally, sensors in the sensor array and particularly the photoactive regions (e.g., regions 213, 215, and 217 of sensors 212, 214, and 216 in FIG. 2) can be made smaller than in current image sensors.

Step 320 of process 300 forms particles of the types intended to create the desired plasmon resonances. Such particles can be metal or composite particles and typically have diameters or other linear dimensions on the order of about 10 nm to 100 nm. The techniques for fabricating the particles will in general depend on the types of particles required. Gold nanoparticles, for example, can be synthesized by chemical reduction of a tetrachloroauric acid (HAuCl4) solution with sodium citrate or sodium borohydride in both aqueous and organic media. Other techniques are known in the art for fabricating gold and other nanoparticles with plasmon resonances.

Step 330 applies the particles produced in step 320 to the sensor array produced in step 310. One technique for particle application in step 330 first mixes each type of particle created in step 320 in a liquid binding material to form an ink for a printing process. For example, particles of a type selected to create a plasmon resonance peaked at a frequency of red light can be suspended in a liquid binding material to form a first type of ink, particles of a type selected to create a plasmon resonance peaked at a frequency of green light can be suspended in a liquid binding material to form a second type of ink, and particles of a type selected to create a plasmon resonance peaked at a frequency of blue light can suspended in a liquid binding material to form a third type of ink. The binding materials can be the same for all particles or may be different. The inks can be applied to the surface of the sensor array using a printing technique such as inkjet printing. In a typical application, each region of bound particles will be about 10 μm or more across, and printed areas of such sizes can be achieved using printing techniques currently used in commercial printers. Smaller printed areas may be achievable with custom ink-jet printers. The liquid binding material can then be dried or cured using heating or other conventional curing processes that depend on the type of binding material used.

An alternative process for applying particles in step 330 can apply a thin layer of an adhesive or binding material to the sensor array. Particles of the different types can then be applied to the respective sensors using a mechanical dispensing system, and the adhesive can be cured to affix the particles. In yet another alternative process, step 330 can deposit a layer of a material such as photoresist containing particles with plasmon resonances on the sensor array and use photolithographic techniques to pattern the layer and control the size and location of particle-containing regions on the photoactive regions of the underlying sensors.

Figure 4:
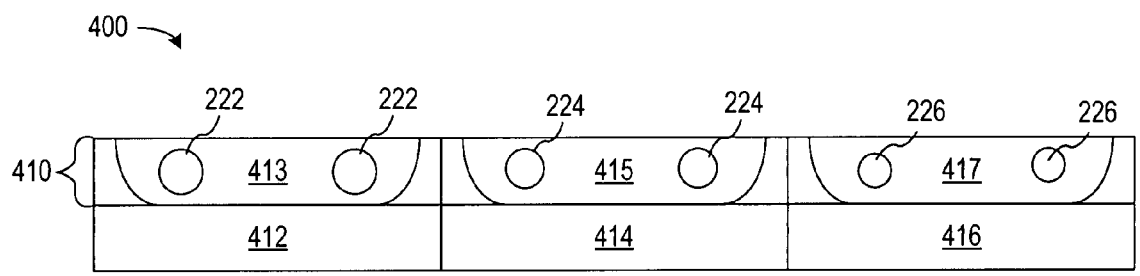
FIG. 4 shows a cross-sectional view of a portion of an image sensor in accordance with an embodiment of the invention using particles embedded in a pixel sensor to enhance sensing of specific frequency bands.

FIG. 4 shows an image sensor 400 in accordance with an embodiment of the invention that embeds particles 222, 224, and 226 in respective pixel sensors 412, 414, and 416. FIG. 4 particularly shows particles 222, 224, and 226 embedded respectively in the photoactive regions 413, 415, and 417 of respective pixel sensors 412, 414, and 416. Alternatively, particles 222, 224, and 226 may be embedded in sensors 412, 414, and 416 adjacent to active regions 413, 415, and 417. As described above, particles 222, 224, and 226 create plasmon resonances that greatly increase the electromagnetic field strength and the efficiency of absorption of photons having frequencies corresponding to the plasmon resonances.

Pixel sensor 400 may be fabricated by mixing particles 222, 224, or 226 in constituents used in fabrication of a layer 410 in which photoactive areas 413, 415, and 417 reside. For example, if layer 410 is an organic semiconductor material, metal particles can be mixed in a liquid that is spun onto an underlying substrate when layer 410 is formed. Alternatively, metal particles may be introduced in a vapor used for epitaxial growth of amorphous silicon or other semiconductor material forming layer 410.

Although the invention has been described with reference to particular embodiments, the description is only an example of the invention's application and should not be taken as a limitation. Various adaptations and combinations of features of the embodiments disclosed are within the scope of the invention as defined by the following claims.

What is claimed is:

1. An image sensor comprising:
   an array of sensors including a first group of the sensors and a second group of the sensors;
   a plurality of first particles, wherein the first particles are positioned to create a first plasmon resonance in the first group of the sensors and thereby enhance sensitivity of the sensors in the first group to electromagnetic radiation having a first frequency that corresponds to the first plasmon resonance; and
   a plurality of second particles, wherein the second particles are positioned to create a second plasmon resonance in the second group of the sensors and thereby enhance sensitivity of the sensors in the second group to electromagnetic radiation having a second frequency that corresponds to the second plasmon resonance.

2. The image sensor of claim 1, further comprising a plurality of third particles, wherein the array of sensors further includes a third group of the sensors, and the third particles are positioned to create a third plasmon resonance in the third group of the sensors and thereby enhance sensitivity of the sensors in the third group to electromagnetic radiation having a third frequency that corresponds to the third plasmon resonance.

3. The image sensor of claim 2, wherein the first frequency, the second frequency, and the third frequency respectively correspond to red light, green light, and blue light.

4. The image sensor of claim 1, wherein the array of sensors is selected from a group consisting of a CCD sensor array and a CMOS sensor array.

5. The image sensor of claim 1, wherein the first particles differ in size from the second particles.

6. The image sensor of claim 1, wherein the first and second particles are spherical, and the first particles have a first diameter that differs from a second diameter of the second particles.

7. The image sensor of claim 1, further comprising:
   a first ink printed on the first group of sensors, wherein the first particles are contained in the first ink; and
   a second ink printed on the second group of sensors, wherein the second particles are contained in the second ink.

* * * * *